United States Patent [19]

Nelson et al.

[11] Patent Number: 4,581,374

[45] Date of Patent: Apr. 8, 1986

[54] CONTACT LENS PRESERVING SOLUTION

[75] Inventors: Eric L. Nelson, Santa Ana; Richard L. Harris, Dana Point, both of Calif.

[73] Assignee: Nelson Research & Development Co., Irvine, Calif.

[21] Appl. No.: 660,024

[22] Filed: Oct. 12, 1984

Related U.S. Application Data

[60] Division of Ser. No. 485,093, Jun. 13, 1983, Pat. No. 4,490,389, which is a continuation of Ser. No. 106,981, Dec. 26, 1979, abandoned, which is a continuation of Ser. No. 941,771, Sep. 13, 1978, abandoned, which is a continuation-in-part of Ser. No. 666,067, Mar. 11, 1976, abandoned.

[51] Int. Cl.⁴ .................. A01N 37/00; A61K 31/19; C11D 3/48
[52] U.S. Cl. .................. 514/574; 252/106; 514/840
[58] Field of Search .............. 514/574, 840; 252/106

[56] References Cited

U.S. PATENT DOCUMENTS

| | | | |
|---|---|---|---|
| 3,065,139 | 11/1962 | Ericson | 167/72 |
| 3,329,607 | 7/1967 | Colobert | 210/61 |
| 3,681,492 | 8/1972 | Kotzbauer | 424/141 |
| 3,689,673 | 9/1972 | Phares, Jr. | 424/326 |
| 3,888,782 | 6/1975 | Boghosian et al. | 252/106 |
| 3,961,933 | 6/1976 | Kuyama et al. | 71/67 |
| 3,983,252 | 9/1976 | Buchalter | 424/333 |

FOREIGN PATENT DOCUMENTS 2532016  7/1975  Fed. Rep. of Germany ............ 4/24

OTHER PUBLICATIONS

Chem. Abst. 91:112,483v (1979)—Nelson Res. Dev.
Chem. Abst. 92:203583q (1980)—Mita et al.
Chem. Abst. 94:90386y (1981)—Nelson et al.
Chem. Abst. 95:1896v (1981)—Nelson Res. Dev.
Y. Saikovs'ka, 63 Chemical Abstracts 47089j; Manufacturing of Eye Drops with Vitamins (1967).
L. Colobert, 59 Chemical Abstracts 1996f; Mechanism of Bacterial Activity on *E. Coli* (1962).

*Primary Examiner*—Douglas W. Robinson
*Attorney, Agent, or Firm*—Knobbe, Martens, Olson & Bear

[57] ABSTRACT

A method for sterilizing contact lenses and especially hydrophilic (soft) contact lenses comprising contacting a contact lens for a period of time sufficient to sterilize the lens with a substantially isotonic, aqueous composition having a pH between 6-9 comprising about 0.01 to about 0.3 percent by weight of an ene-diol compound and from about 0.1 to about 25 ppm copper ion. Preferred ene-diol compounds are dihydroxyfumaric acid and dihydroxymaleic acid.

12 Claims, No Drawings

CONTACT LENS PRESERVING SOLUTION

RELATION TO EARLIER FILED APPLICATIONS

This application is a division of application Ser. No. 485,093, filed June 13, 1983, now U.S. Pat. No. 4,490,389 which is a continuation of application Ser. No. 106,981, filed Dec. 26, 1979, now abandoned, which is in turn a continuation of application Ser. No. 941,771, filed Sept. 13, 1978, now abandoned, which is in turn a continuation-in-part of application Ser. No. 666,067 filed Mar. 11, 1976, now abandoned.

BACKGROUND OF THE INVENTION

1. Field of the Invention

The invention relates generally to the preservation of contact lenses. More particularly, the present invention relates to a method and composition for sterilizing plastic hydrophilic or "soft" contact lenses.

2. Background of the Prior Art

Hydrophilic or partially hydrophilic plastic materials have been described for use in making so-called soft contact lenses. For example, U.S. Pat. No. 3,503,393 to Seiderman and U.S. Pat. No. 2,976,576 to Wichterle describe processes for producing three-dimensional hydrophilic polymers of polyhydroxy-ethylmethacrylate in aqueous reaction media having a sparingly cross-linked polymeric hydrogel structure and having the appearance of elastic, soft, transparent hydrogels. Other soft contact lenses include lenses made out of other optically suitable materials.

The main virtues of these lenses are their softness and optical suitability. The hydrophilic lenses are particularly useful in ophthalmology due to their remarkable ability to absorb water with concomitant swelling to a soft mass of extremely good mechanical strength, complete transparency and the ability to retain shape and dimensions when equilibrated in a given fluid.

One of the problems connected with these soft contact lenses is the method of their sterilization and cleaning. The very property of the hydrophilic soft lenses which allows them to absorb up to 150 percent by weight of water also allows preservatives which might otherwise be used for cleaning and sterilization to be absorbed and even concentrated and later released when the soft contact lens is on the eye. The release may be much slower than the uptake, thereby allowing the preservative to build up in the lenses. This buildup eventually affects the physical characteristics of the lenses including dimension, color, etc. This can have the harmful result of damaging or staining the contact lens itself and/or harming the sensitive tissues of the conjunctivae or cornea.

Hard contact lenses do not absorb appreciable amounts of water (i.e. 0.1–0.4%) and thus the use of effective preservatives generally does not create a problem in the hard contact lens field. Sterilization of hydrophilic soft contact lenses is carried out by procedures described in U.S. Pat. Nos. 3,689,673 or 3,888,782 or more generally by boiling the lenses in normal saline. Furthermore, users of soft contact lenses are warned that under no circumstances should solutions designed for hard contact lenses be used, for the reason that the preservatives in such solutions will be absorbed and even concentrated by the soft lens and may seriously damage the soft lens and/or the eye of the user. In this connection, U.S. Pat. No. 3,689,673 further discloses that a number of commonly used antimicrobial agents are concentrated in the soft lens and suggests that these materials may cause corneal damage and that similar in vitro and in vivo tests have shown the undesirability of such antimicrobial agents when used with hydrophilic lenses.

It is also known that the relatively rapid oxidation of an ene-diol compound effects substantially a complete kill of microorganisms which are in contact with it. Ordinarily, the oxidation of an ene-diol compound occurs too slowly to be effective as a microbicide. However, some metal ions, notably copper ions, catalyze the reaction so that it takes place rapidly and thereby is effective as a microbicide, e.g. see U.S. Pat. No. 3,065,139.

Commercial utility of the rapid oxidation of an ene-diol compound to obtain the benefit of its microbicidal effect is difficult because the reaction takes place so quickly when the necessary ingredients are in contact with each other that commercially packaged products do not have useful shelf life. U.S. Pat. No. 3,681,492 deals with compositions in which the rate of oxidation of ene-diol is inhibited or retarded so that the microbicidal effect is sustained for a longer period. However, even the retarded compositions generally are not useful as commercial products because the reaction can only be retarded for a relatively short time, for example a matter of days, which is not long enough to provide a suitable shelf life for a commercial product. In addition, a highly retarded reaction does not produce as intense an antimicrobial effect as a mildly retarded reaction or one which is not retarded. Other problems with the foregoing ene-diol reaction are that the breakdown products of common ene-diols, e.g. ascorbic acid, form a brownish color in solution and the copper ions in solution react with each other to form a red copper metal precipitate. Both of these problems render the prior art formulation unfit for use in preserving hydrophilic contact lenses.

SUMMARY OF THE INVENTION

It has now been discovered that hydrophilic (soft) contact lenses may be effectively sterilized and used without deleterious effect to the lenses or the eyes of the user by the present invention. The sterilizing solution of this invention will not be absorbed by the lenses in significant quantities. In addition, to the extent, if any, that the sterilizing solution of this invention is absorbed by the lenses, it will not harm the lenses or the eyes of the wearer. This invention also solves the shelf life problem discussed above as well as the discoloration and precipitate problem.

The present invention relates to a method for sterilizing hydrophilic (soft) contact lenses comprising contacting a hydrophilic (soft) lens for a period of time sufficient to sterilize the lens with a substantially isotonic, aqueous composition comprising about 0.01 to about 0.3 percent by weight of an ene-diol compound and sufficient water soluble copper-containing compound to supply between 0.1 and 25 ppm copper ion.

The invention also relates to a method for sterilizing plastic hydrophilic soft contact lenses comprising forming a microbicidal solution by combining a microbicidal amount of an ene-diol in a dissolvable or dispersable solid unit dosage form with an aqueous diluent containing between about 0.1 and about 25 ppm of copper ions and contacting a plastic hydrophilic soft contact lens with said microbicidal solution for a period of time sufficient to sterilize the lens.

One of the essential ingredients of this invention is an ene-diol compound. Typical ene-diol compounds are ascorbic acid compounds, reductic acid compounds, squaric acid compounds, dihydroxymaleic acid compounds and dihydroxyfumaric acid compounds. Typical examples of the foregoing ene-diol compounds are ascorbic acid itself, salts of ascorbic acid such as sodium ascorbate, ascorbic acid esters such as ascorbyl palmitate and any other ascorbic acid derivatives that retain the ene-diol molecular structure. The comparable acid, salt and ester forms of the other ene-diols described herein may also be used in this invention. Mixtures of ene-diols may also be used. The preferred ene-diols are ascorbic acid and dihydroxymaleic acid and their salts, e.g., sodium or potassium. The total amount of ene-diol which should be used in the present invention varies from about 0.01 to about 0.3 by weight of the total composition and preferably about 0.05 to about 0.1% by weight of the total composition.

Another of the essential ingredients of this invention is copper. Preferably, copper is used in the form of water soluble cupric compounds; and the particularly preferred copper-containing compound is cupric chloride or cupric sulfate because both are highly soluble in water, relatively material, and readily available. The anhydrous or hydrate, e.g., monohydrate, or dihydrate forms of cupric chloride also may be used, the anhydrous form being preferred for solid dosage forms. Water insoluble copper compounds, e.g., cupric acetylacetonate and cupric oleate, also may be used provided cupric ions become available in the final composition.

The limitations on the amounts of copper and ene-diol are critical. If greater amounts of copper are used, a red copper precipitate is formed. If greater amounts of ene-diol are used, the resulting solution becomes discolored, especially if ascorbic acid is used as the ene-diol. This is because Applicants have discovered that the ene-diols which may be used in this invention do not all act the same. That is, Applicants have discovered that the ene-diol, dihydroxymaleic acid and its ester and salts are unique in that aqueous solutions of this ene-diol are essentially colorless and that other ene-diols, notably ascorbic acid, tend to form yellow-brown solutions in water which are undesirable from a commercial point of view and which may tend to adversely affect the soft lenses over a long period of time. In addition, the pH of the solution is critical. If the solution pH is outside the range of pH 6–9, the lenses are adversely affected.

DETAILED DESCRIPTION OF THE INVENTION

One preferred embodiment of the invention is a combination of dry, solid, water soluble or dispersible unit dosage forms, e.g., tablets. One type of tablet would contain the ene-diol and a second type of tablet would contain the copper. Upon combining the tablets in a predetermined amount of water, the proper concentration of all of the active ingredients is achieved.

In a second preferred embodiment, the ene-diol is formulated in an aqueous, preserved diluent and the copper is in the form of a water soluble tablet or other solid dosage form. Prior to use, the tablet is dissolved in the diluent to form the microbicidal solution for sterilizing contact lenses.

A typical composition of the present invention may contain in addition to the active ingredients described earlier, buffers stabilizers and isotonic agents which aid in making the ophthalmic composition more comfortable to the user. These additional materials must not distort the soft lens. In this regard we have found that Polysorbate 80 and Brij 58 act to stabilize the aqueous formation in amounts ranging from about 0.05 to about 0.6 and preferably about 0.2% (w/v).

Suitable buffers include sodium or potassium citrate, citric acid, boric acid, various mixed phosphate buffers including combinations of $Na_2HPO_4$, $NaH_2PO_4$, $K_2HPO_4$, $KH_2PO_4$ and $KHCO_3$. Generally, buffers may be used in amounts ranging from about 0.0 to 2.5 and preferably 0.1 to 2.0% (w/v). The potassium salts of buffers are preferred when using dihydroxymaleic or dihydroxy fumaric acid as the ene-diol in the composition. Potassium salts of these acids were found to be water soluble to a much greater extent than the corresponding sodium salts.

The treating solution for soft contact lenses should be maintained at an osmotic pressure similar to that of physiologic saline, i.e., substantially isotonic, or approximately 0.9% saline, or with suitable agents alone or in combination to render the solution substantially isotonic. Hypotonic solutions, e.g., tap water, will cause the lens to adhere tightly to the cornea, while hypertonic solutions (excess saline) will result in stinging, lacrimation and a red eye.

If solid dosage forms are used, the formulation may include conventional lubricants, binders, and excipients which include glycerol, sorbitol, boric acid, propylene glycol, polyethylene glycols, dextran and methylcellulose. These materials are used in amounts varying between 0.01 and 10 and preferably between about 0.1 and 5 weight percent.

If a sustained microbicidal effect is desired, an amine-containing inhibitor can be included in the composition to retard the rate of reaction of the degree desired. The preferred amine-containing inhibitor is tromethamine, although any of the amines disclosed in U.S. Pat. No. 3,681,492 may be employed. The inhibitor may be included either in one of the solid dosage forms containing the ene-diol compound or the copper compound.

Ingredients which aid in dispersing the various ingredients throughout a body of water into which they are introduced may be useful in the compositions of this invention. The above-mentioned sodium bicarbonate and organic acid mixtures are useful as such dispersants. For different bulk materials it may be desirable to employ conventional disintegrators such as "Veegum HV," methylcellulose, starch, sugar, etc. within the granules to aid in the speed and effectiveness of dissolving or dispersing them throughout the water into which the composition is introduced. For purposes of this disclosure, the word "dissolving" is used functionally to mean dissolving or dispersing.

The method of use of the sterilizing and cleaning solution is the following. The lenses are first rinsed with a few drops of the subject solution or saline to remove surface contaminants such as mucous, eye makeup, etc., and then placed in a suitable container with sufficient amount of the subject solution to cover the lenses. The lenses are allowed to soak for at least about 10 minutes and up to 8 hours to achieve substantial kill of spores, fungi and yeasts. This soaking has been shown to effectively sterilize the lenses. The foregoing method is carried out at ambient temperature or elevated temperatures, i.e., about 40°–100° C.

The word "sterilize" is used in the present invention to mean the rendering non-viable of substantially all pathogenic microbes, including Gram negative and Gram positive bacteria as well as fungi.

The term "microbicide" is used in the present invention to mean a composition which renders non-viable all microorganisms including, but not limited to, bacteria, fungi, yeasts and viruses.

To illustrate the manner in which the invention may be carried out, the following examples are given. It is understood however, that the examples are for the purposes of illustration and the invention is not to be regarded as limited to any of the specific materials or conditions set forth therein. Unless otherwise stated, "%" means weight per unit volume expressed as a percent "(w/v)."

EXAMPLE I

A number of different compositions were made by blending various ingredients to form clear diluents to which an ene-diol compound was added to produce the sterilizing solution. The following table sets forth the composition of various sterilizing solutions.

TABLE 1

| Ingredient | % Weight | | | | |
|---|---|---|---|---|---|
| | 1 | 2 | 3 | 4 | 5 |
| Part A | | | | | |
| Ammonium Chloride | 0.025 | 0.025 | 0.025 | 0.025 | 0.025 |
| Cupric Chloride dihydrate | 0.005 | 0.005 | 0.005 | 0.005 | 0.005 |
| Potassium Phosphate, monobasic | 0.530 | 0.530 | 0.530 | 0.530 | 0.530 |
| Potassium Phosphate, dibasic | 1.060 | 1.060 | 1.060 | 1.060 | 1.060 |
| Potassium Chloride | 0.300 | 0.300 | 0.300 | 0.300 | 0.300 |
| Water | 97.880 | 97.880 | 97.820 | 97.842 | 97.820 |
| Part B | | | | | |
| Dihydroxymaleic acid | 0.200 | | | | |
| Dihydroxyfumaric acid | | 0.200 | | | |
| Reductic acid | | | 0.260 | | |
| Ascorbic acid | | | | 0.238 | |
| Squaric acid | | | | | 0.260 |

When tested against microorganisms, these compositions were found to be effective as a microbicide.

EXAMPLE II

Example I was repeated, except various salts of dihydroxymaleic acid were combined in separate instances with the diluent to produce the sterilizing solution. The following table sets forth the composition of typical sterilizing solutions.

TABLE 2

| Ingredient | % Weight | | |
|---|---|---|---|
| | 1 | 2 | 3 |
| Part A | | | |
| Ammonium chloride | 0.025 | 0.025 | 0.025 |
| Cupric chloride dihydrate | 0.005 | 0.005 | 0.005 |
| Potassium phosphate, monobasic | 0.530 | 0.530 | 0.530 |
| Potassium phosphate, dibasic | 1.060 | 1.060 | 1.060 |
| Potassium chloride | 0.100 | 0.100 | 0.100 |
| Water | 97.975 | 98.018 | 98.060 |
| Part B | | | |
| Dihydroxymaleate dipotassium salt | 0.305 | | |
| Dihydroxymaleate disodium salt | | 0.262 | |
| Dihydroxymaleate dilithium salt | | | 0.220 |

When tested against microorganisms, these compositions were found to be effective as a microbicide.

EXAMPLE III

The effectiveness of composition 1 in Table 1 of Example I as a microbicide for contact lens sterilization was determined. Contact lenses were dipped in bacterial cultures of $10^8$ organisms per milliliter of either staphylococcus or pseudomonas. Upon removal it was shown that $10^7$ organisms per milliliter remained in contact with the lenses and the test lenses were then soaked in said composition and control lenses in sterile saline solution. At specific time intervals, bacterial counts were made on the lenses removed from the soaking solutions and rinses with sterile saline. The results of the study are shown in Table 3.

TABLE 3

| Lens | Bacterial Culture | Bacterial count at time of removal | | |
|---|---|---|---|---|
| | | t = 10 mins | t = 20 mins | t = 30 mins |
| 1 | Staphylococcus | <$10^5$ | | |
| 2 | Pseudomonas | <$10^5$ | | |
| 3 | Staphylococcus | | <$10^3$ | |
| 4 | Pseudomonas | | <$10^3$ | |
| 5 | Staphylococcus | | | <$10^2$ |
| 6 | Pseudomonas | | | <$10^2$ |
| 7 | Control | >$10^7$ | | |
| 8 | Control | | >$10^7$ | |
| 9 | Control | | | >$10^7$ |

The results show that said composition is effective as a microbicide when sterilizing contact lenses.

EXAMPLES IV

Example I was repeated, except the individual parts A and B were pressed into tablet form. The result was that one tablet of part A and one tablet of part B were added to the water to obtain the sterilizing solutions. Comparable results were obtained.

EXAMPLE V

1. Solution

The following aqueous composition containing 25 ppm copper ion was prepared by adding the ingredients listed below (in order listed) to 900 ml H$_2$O followed by sterile filtering. The pH of the resulting solution was 7.7.

| | grams |
|---|---|
| CuSO$_4$.5H$_2$O | 0.0098 |
| B(OH)$^3$ | 0.50 |
| Potassium Sorbate | 0.134 |
| Tromethamine | 0.15 |
| NaCl | 0.58 |
| H$_2$O | to 1000 ml |

2. Tablet

The following tablets were made by mixing the ingredients listed below in a mortar and grinding. The resulting powder was dried in a vacuum oven at 50° C. for 3 hours at 30–50 mm Hg. The resulting dried powder was removed from the oven and briefly reground. The resulting material was formed into 100 mg tablets using a Colton single punch tablet press.

|  | grams |
| --- | --- |
| Ascorbic acid | 7.5 |
| L-tartaric acid | 24.0 |
| Na$_2$CO$_3$ | 20.0 |
| Lactase | 46.5 |
| PEG 4000 | 2.0 |
| TOTAL | 100.0 grams |

3. In order to test for microbicidal activity, one tablet was dissolved in 10 ml of solution (to give 0.075% ascorbic acid in solution) and tested as in Example II except that the following microorganisms were used: *Serratia marcescens, Staphylococcus aureus, Pseudomonas aeruginosa, Escherichia coli, Candida albicans, Aspergillus niger* at contact times of 2, 4 and 6 hours. Initial counts of $10^5$–$10^6$ for each microorganism were reduced to less than $10^2$ counts for all microorganisms (except *A. niger*) within 2 hours and *A. niger* was reduced to less than $10^2$ within 6 hours.

In addition, no red precipitate or discoloration was noted. Subsequent analysis of the lenses used in the study showed that no changes in size had occurred.

We claim:

1. A method for sterilizing contact lenses, comprising:
    contacting a hydrophilic soft contact lens with an aqueous composition for a period of time sufficient to sterilize the lens;
    said composition having a pH between about 6 and 9 comprising at least 0.01 percent by weight of an ene-diol compound, which is dihydroxymaleic acid, dihydroxyfumaric acid, or an ester or salt thereof; and at least 0.1 ppm copper ion in solution.

2. The method of claim 1, wherein the copper ion is supplied by cupric chloride.

3. The method of claim 1, wherein the composition includes a water soluble amine which forms a complex with said copper ion in aqueous solution.

4. The method of claim 3, wherein the amine is tromethamine.

5. The method of claim 1, wherein the composition is substantially isotonic.

6. The method of claim 1, further comprising the step of preparing the aqueous composition by dissolving a premeasured portion of a dihydroxymaleic acid compound and a premeasured portion of a water soluble copper salt in water.

7. The method of claim 6, wherein the composition is substantially isotonic.

8. The method of claim 1, wherein the ene-diol compound is dihydroxymaleic acid or an ester or salt thereof.

9. The method of claim 1, wherein the ene-diol compound is dihydroxyfumaric acid or an ester or salt thereof.

10. The method of claim 1, wherein the composition comprises between about 0.01 and about 0.3 percent by weight of the ene-diol compound, and between about 0.1 and about 25 ppm copper ion.

11. The method of claim 10, wherein the ene-diol compound is dihydroxymaleic acid or an ester or salt thereof.

12. The method of claim 10, wherein the ene-diol compound is dihydroxyfumaric acid or an ester or salt thereof.

* * * * *